US007238376B2

(12) United States Patent
Chen et al.

(10) Patent No.: US 7,238,376 B2
(45) Date of Patent: Jul. 3, 2007

(54) BLACK TEA EXTRACT FOR PREVENTION OF DISEASE

(75) Inventors: Kuang Yu Chen, Belle Mead, NJ (US); Chi-Tang Ho, East Brunswick, NJ (US); Robert T. Rosen, Monroe Township, NJ (US); Geetha Ghai, Murray Hill, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 10/870,187

(22) Filed: Jun. 17, 2004

(65) Prior Publication Data

US 2004/0224034 A1    Nov. 11, 2004

Related U.S. Application Data

(63) Continuation of application No. 09/992,860, filed on Nov. 14, 2001.

(60) Provisional application No. 60/248,942, filed on Nov. 15, 2000.

(51) Int. Cl.
*A01N 65/00* (2006.01)
*A01N 31/35* (2006.01)
(52) U.S. Cl. .................... 424/729; 424/736; 514/456
(58) Field of Classification Search ............. 424/729, 424/736; 514/886, 825, 456
See application file for complete search history.

(56) References Cited

U.S. PATENT DOCUMENTS

| 5,104,901 | A | | 4/1992 | Shimamura et al. |
| 5,605,929 | A | * | 2/1997 | Liao et al. |
| 5,989,557 | A | | 11/1999 | Bombardelli et al. |
| 6,096,359 | A | | 8/2000 | Bombardelli et al. |
| 6,410,061 | B1 | | 6/2002 | Morre et al. |

FOREIGN PATENT DOCUMENTS

| DE | 19627344 A1 * | 1/1998 |
| DE | 10016771 | 10/2002 |
| EP | 0853943 | 7/1998 |
| JP | 02-053717 | 2/1990 |
| JP | 06-009391 | 1/1994 |
| JP | 08245412 A * | 9/1996 |
| JP | 09-227374 | 9/1997 |
| JP | 10-072361 | 3/1998 |
| WO | WO 99/01148 | 1/1999 |
| WO | WO 99/08693 | 2/1999 |
| WO | WO 00/74662 | 12/2000 |
| WO | WO 01/03716 | 1/2001 |
| WO | WO 01/21137 | 3/2001 |
| WO | WO 01/21165 | 3/2001 |
| WO | WO 01/49285 | 7/2001 |

OTHER PUBLICATIONS

Katiyar, S. K. et al. Carcinogenesis (1997), 18: 1911-1916. Inhibition of phorbol ester tumor promoter 12-O-tetradecanoylphorbol-13-acetate-caused inflammatory responses in SENCAR mouse skin by black tea polyphenois.*
de Maat et al., "Consumption of black and green tea had no effect on inflammation, haemostasis and endothelial markers in smoking healthy individuals", Eur J Clin Nutr. Oct. 2000;54(10):757-763.
Katiyar et al., "Tea antioxidants in cancer chemoprevention", J Cell Biochem Suppl. 1997;27:59-67.
Lin et al., "Theaflavin-3,3'-digallate from black tea blocks the nitric oxide synthase by down-regulating the activation of NF-κB in macrophages", Eur J Pharmacol. Feb. 19, 1999;367(2-3):379-388.
Miller et al., "The antioxiadant properties of theaflavins and their gallate esters—radical scavengers or metal chelators?", FEBS Lett. Aug. 19, 1996;392(1):40-44.
Rogers et al., "Black tea and mammary gland carcinogenesis by 7,12-dimethylbenz[a]anthracene in rats fed control or high fat diets", Carcinogenesis. Jul. 1998;19(7):1269-1273.
Shiraki et al., Antioxidative and antimutagenic effects of theaflavins from black tea. Mutat Res. Jan-Feb 1994;323(1-2):29-34.
Stoner and Mukhtar, "Polyphenols as cancer chemopreventive agents", J Cell Biochem Suppl. 1995;22:169-180.
Wiseman et al., "Antioxidants in tea", Crit Rev Food Sci Nutr. Dec. 1997;37(8):705-718.
Yang et al., "Tea and tea polyphenols in cancer prevention", Symposium: Diet, Natural Products and Cancer Prevention: Progress and Promise. 2000, pp. 472S-478S, American Society for Nutritional Sciences.
Yoshida et al., "Inhibitory effect of tea flavonoids on the ability of cells to oxidize low density lipoprotein", Biochem Pharmacol. Dec. 1, 1999;58(11):1695-1703.
Chen et al. Alteration of gene expression in normal-appearing colon mucosa of APC(min) mice and human cancer patients. Cancer Res. May 15, 2004;64(10):3694-700.
Drexler et al. Leukemia cell lines: in vitro models for the study of acute promyelocytic leukemia. Leuk Res. Oct. 1995;19(10):681-91. Review.
Huang et al., Effect of black tea theaflavins on 12-O-tetradecanoylphorbol-13acetate-induced inflammation. Ch. 24 of Herbs: Challenges in Chemistry and Biology: Wang et al. eds. American Chemical Society, 2006, Washington, DC, pp. 314-325.
Jax®Mice Data Sheet : C57BL/6J-$Apc^{Min}$/J stain. Information provided by "The Jackson Laboratory" website regarding mouse strain C57BL/6J-$Apc^{Min}$/J.
Lu et al. Differential effects of theaflavin monogallates on cell growth, apoptosis, and Cox-2 gene expression in cancerous versus normal cells. Cancer Res. Nov. 15, 2000;60(22):6465-71.
Sacks PG. Cell, tissue and organ culture as in vitro models to study the biology of squamous cell carcinomas of the head and neck. Cancer Metastasis Rev. Mar. 1996;15(1):27-51. Review.

* cited by examiner

*Primary Examiner*—Michele Flood
(74) *Attorney, Agent, or Firm*—Jones Day

(57) ABSTRACT

Compositions and methods for preventing and treating disease are provided. The compositions are extracts of black tea that include a mixture of theaflavin-3-gallate and theaflavin-3'-gallate.

15 Claims, No Drawings

BLACK TEA EXTRACT FOR PREVENTION OF DISEASE

This application is a continuation of U.S. application Ser. No. 09/992,860, filed Nov. 14, 2001, which claims the benefit of U.S. Provisional Application No. 60/248,942, filed Nov. 15, 2000.

BACKGROUND OF THE INVENTION

Epidemiological studies have suggested that tea may have a protective role in disease, including certain human cancers. Catechin polyphenols isolated from green tea have been shown to inhibit proliferation of cultured mammalian cells including colon carcinoma, lung carcinoma, breast carcinoma, melanoma, and leukemic cells (Lea, M. A. et al. 1993. *Cancer Lett.* 68:231-236; Valcic, S. et al. 1996. *Anticancer Drugs* 7:461-468). It has been reported that a major green tea catechin polyphenol, (−)epigallocatechin gallate (EGCG), inhibits growth of human tumor cells, including Caco-2 colorectal cancer cells, Hs578T breast cancer cells, and SV40-transformed W138 cells, but has little or no inhibitory effect on the growth of their normal counterparts (Chen, Z. P. et al. 1998. *Cancer Lett.* 129:173-179).

Black tea extracts have also been shown to be potent in inhibiting tumorigenesis in several animal model systems, including skin (Javed, S. et al. 1998. *Biomed. Environ. Sci.* 11:30-7-313), lung (Yang, G. Y. et al. 1997. *Carcinogenesis* 18:2361-2365), colon (Weisburger, J. H. et al. 1998. *Carcinogenesis* 19:229-232), esophagus (Morse, M. A. et al. 1997. *Nutr. Cancer* 29:7-12), and mammary gland (Rogers, A. E. et al. 1998. *Carcinogenesis* 19:1269-1273). The major black tea polyphenols have been characterized to be theaflavin (TF-1), theaflavin-3-gallate and theaflavin-3'-gallate mixture (TF-2), and theaflavin-3,3'-digallate (TF-3). These theaflavin polyphenols are fermentation products derived from green tea polyphenols and are responsible for the characteristic color, fragrance and taste of black tea.

The biological effects of each individual black tea polyphenol have not been well-studied in terms of their molecular mechanisms. TF-3 has been shown to be as potent as EGCG from green tea inhibiting the growth of human A431 carcinoma cells and in reducing autophosphorylation of EGF and PDGF receptors (Liang, Y. C. et al. 1999. *Carcinogenesis* 20:733-736). There are no reports of the activity of any other black tea polyphenols.

SUMMARY OF THE INVENTION

An object of the present invention is an extract of black tea which comprises a theaflavin-3-gallate and a theaflavin-3'-gallate mixture. Also included in the present invention is a composition which comprises the black tea extract in combination with at least one other compound selected from a rosemary extract, a Mexican Bamboo extract, a Huzhang extract, resveratrol, a green tea extract, an orange peel extract, and a hydroxylated or methoxylated resveratrol analog.

Another object of the present invention is a method for inhibiting tumor cell growth in an animal which comprises administering to an animal the extract of black tea.

Yet another object of the present invention is a method for preventing or treating disease associated with Cox-2 gene expression in an animal which comprises administering to an animal an effective amount of an extract of black tea and wherein the disease is selected from the group consisting of cancer, inflammation, and arthritis. Also included in the present invention is a method wherein the black tea extract is administered in combination with at least one additional compound selected from a rosemary extract, a Mexican Bamboo extract, a Huzhang extract, resveratrol, a hydroxylated resveratrol analog, a green tea extract, an orange peel extract or a methoxylated resveratrol analog.

DETAILED DESCRIPTION OF THE INVENTION

The black tea polyphenol extract known as TF-2, a mixture of theaflavin-3-gallate and theaflavin-3'-gallate, has been found to inhibit both cancer cell growth and apoptosis in cancer cells. None of the other black tea polyphenols tested showed this activity. Additionally, TF-2 was shown to specifically inhibit expression of the Cox-2 gene, a gene known to be associated with both inflammatory reactions and carcinogenesis, at both the mRNA and protein level. The present invention provides both compositions and methods for prevention and treatment of disease, including cancer.

The effects of black tea polyphenols on proliferation of W138 and W138VA cells was examined. W138 diploid fibroblasts have a finite life span whereas the virally transformed W138VA cells are cancerous in nude mice. Both cell types were grown in 24 well plates in the presence of increasing doses of the theaflavin polyphenols, TF-1, TF-2 and TF-3 (0, 1, 5, 10, 25 and 50 µM). Viable cells were stained with crystal violet 4 days after plating. A decrease in staining intensity relative to the untreated control cells were indicative of growth inhibition by the polyphenol compound. Of the three theaflavin polyphenols tested, only TF-2 had significant effects on cells growth. Growth of W138VA cells was inhibited significantly by TF-2 at doses in the range of 10 to 50 µM, while there was no significant effect on cell growth in W138 cells. The other 2 polyphenols tested did not exhibit this differential growth inhibition of W138 versus W138VA cells. The $IC_{50}$ value for TF-2 and growth inhibition of W138VA cells was estimated to be 3 µM.

To determine whether the differential inhibitory effect of TF-2 is general for other types of cancerous cells, the effects of TF-2 on Caco-2 colorectal cancer cells were examined and compared with effects of TF-2 in their normal counterpart, CCD-33Co colorectal cells. In control cells, there was a slight decrease in the density of cells in the CCD-33Co culture in the presence of the highest dose of TF-2 only, 50 µM. In contrast, the presence of TF-2 at wither 10 or 50 µM in Caco-2 cultures resulted in a significant reduction of cell number as well as a dramatic morphological change in the cells. These data demonstrate that TF-2 has effects to inhibit cell growth in more than one type of cancer cell.

Since apoptosis is a major cause underlying growth inhibition in cells, the effects of TF-2 on apoptosis induction in transformed cells was examined using a TUNEL (terminal deoxynucleotidyl transferase-mediated dUTP nick-end labeling) assay. It has been reported that theaflavin and theaflavin digallate can induce apoptosis in human lymphoid leukemia cells and human stomach tumor cells (Hibasami, H. et al. 1998. *Int. Mol. Med.* 1:725-727). Using the TUNEL assay, TF-2 treatment (100 µM for 18 hours) caused almost every cell in the W138VA culture to exhibit apoptosis, as indicated by green fluorescence in the assay. In contrast, almost no cells in the normal W138 culture exhibited green fluorescence after TF-2 treatment. DNA fragmentation analysis was then performed to determine the time course of the apoptotic effect. DNA fragmentation was observed within 4 hours following TF-2 treatment in W138VA cells. There was no significant DNA fragmentation in TF-2-treated W138 cells over a 24 hour period. These results indicate that transformed W138VA cells had a greater propensity for apoptosis in response to TF-2 as compared to non-transformed cells (W138). This observation likely accounts at least in part for the differential inhibitory effect of TF-2 in the growth of transformed cancerous cells.

As a result of the significant effects of TF-2 on growth of Caco-2 cells in culture, the potential role of the Cox-2 gene in the growth suppressive effects of cancerous colon cells was examined. Cox-2 gene expression has been shown to be linked to the development of colon cancer, with increased expression observed in about 90% of human colorectal cancers and 40% of premalignant colorectal adenomas (Eberhart, C. E. et al. 1994. *Gastroenterology* 107:1183-1188). A direct link between Cox-2 expression level and polyps formation has been demonstrated in APC knockout mice, indicating a direct role for this gene in colon cancer formation (Oshima, M. et al. 1996. *Cell* 87:803-809). The Cox-2 gene encodes an inducible form of cyclooxygenase that has been shown to be a key enzyme in prostaglandin biosynthesis. Therefore, the effect of black tea polyphenols on Cox-2 expression was examined.

All three polyphenols were tested, TF-1, TF-2 and TF-3. Of the three compounds tested, only TF-2 significantly suppressed Cox-2 gene expression in Caco-2 cells. Effects were seen at doses of 50 to 100 μM TF-2. Despite their structural similarity, both TF-1 and TF-3 failed to affect Cox-2 gene expression. The green tea polyphenol EGCG was also tested and although it suppressed Cox-2 gene expression it was not as potent as TF-2.

The effect of TF-2 on the time course of Cox-2 gene expression in Caco-2 cells was then examined. Cox-2 mRNA was detectable in quiescent Caco-2 cells, consistent with the finding that colon cancer cells have elevated Cox-2 gene expression. Fresh serum induced a 2- to 4-fold increase in Cox-2 expression in Caco-2 cells as early as 4 hours after stimulation; this was expected because of the known stimulatory effects of serum factors. The presence of TF-2 during serum stimulation, however, not only completely blocked the serum-induced increase in Cox-2 gene expression but also abolished the basal level of Cox-2 mRNA.

The effect of TF-2 on Cox-2 gene expression was also examined in W138 and W138VA cells following serum stimulation. Unlike Caco-2 cells, no Cox-2 mRNA was detectable in quiescent W138 or W138VA cells. However, serum stimulation significantly induced the production of a 4.5 kb Cox-2 transcript in both W138 and W138VA cells within 4 hours of stimulation. The levels of induced Cox-2 mRNA in W138VA cells were higher and more sustained than that seen in W138 cells, suggesting that Cox-2 may be more stable in transformed cells. In both transformed and non-transformed cells, TF-2 blocked the serum-induced increase in Cox-2 gene expression. To demonstrate that the inhibition of expression resulted in a decrease in Cox-2 protein product, the relative levels of Cox-2 protein was measured in W138 and W138VA cells. TF-2 treatment produced a substantial decrease ion the levels of Cox-2 protein in both W138 and W138VA cells. TF-2 at a concentration of 40 μM reduced the Cox-2 protein level in W138 cells by about 50% and completely eliminated Cox-2 protein levels in W138VA cells.

To determine whether the effect of TF-2 on Cox-2 gene expression was specific for this gene or part of a global suppression of serum inducible genes, the effects of TF-2 on the expression of several other genes were determined (e.g., c-fos, c-myc, thymidine kinase, BRCA1, BRCA2, PCNA, Cox-1). Of the genes examined, the only one affected significantly by TF-2 was Cox-2. Expression of the Cox-1 gene was completely unaffected by TF-2, indicating that the effects of TF-2 were Cox-2-specific.

The data provided herein for black tea extracts, specifically TF-2, support the development of foods and dietary supplements which comprise TF-2 for animal consumption. For purposes of the present invention by "animal" it is meant to include humans. These foods and supplements are referred to by those of skill in the art as "nutraceuticals". Based upon the experiments described herein, it is expected that compositions comprising TF-2 will be useful as nutraceuticals for prevention or treatment of cancer, as well as for other diseases associated with Cox-2 including but not limited to inflammation and arthritis. One of skill can use the results of experiments in cells and animals described herein to determine effective amounts to be administered to other animals, including humans. By "effective amount" it is meant a concentration that inhibits tumor growth, or another appropriate pharmacological endpoint, either in vitro in cells or in vivo in animals. For example, human test doses can be extrapolated from effective doses in cell studies, such as $IC_{50}$ values, or from effective doses in vivo by extrapolating on a body weight or surface area basis. Such extrapolations are routine in the art.

Compositions comprising TF-2 can be formulated for administration as a food supplement using one or more fillers. Alternatively, compositions comprising these extracts can be administered as conventional pharmaceuticals using one or more physiologically acceptable carriers or excipients. Nutraceutical compositions can be formulated for administration by any route including, but not limited to, inhalation or insufflation (through mouth or nose), oral, buccal, parenteral, vaginal, or rectal administration. In one embodiment, oral administration, the compositions are added directly to foods and ingested as part of a normal meal. Various methods are known to those skilled in the art for addition or incorporation of nutraceuticals into foods.

Compositions for use in the present invention can also be administered in the form or tablets or capsules prepared by conventional means with pharmaceutically acceptable excipients such as binding agents, fillers, lubricants, disintegrants, or wetting agents. Examples of specific compounds for use in formulating tablets and capsules are described in detail in the U.S. Pharmacopeia. Tablets comprising the extract can also be coated by methods well known in the art. Liquid preparations for oral administration can also be used. Liquid preparations can be in the form of solutions, syrups or suspensions, or a dry product for reconstitution with water or another suitable vehicle before use. Such liquid preparations can be prepared by conventional means with pharmaceutically acceptable additives such as suspending agents, emulsifying agents, non-aqueous vehicles, and preservatives. Again, specific additives are well known to those of skill and are listed in places such as the U.S. Pharmacopeia. In one embodiment, the oral preparation is formulated to provide controlled time release of the active nutraceutical components. For buccal administration the extract can be formulated as a tablet or lozenge.

For administration by inhalation, compositions for use in the present invention can be delivered in the form of an aerosol spray in a pressurized package or as a nebulizer, with use of suitable propellants. In the case of a pressurized aerosol, the dosage unit can be determined by providing a valve to deliver a metered dose.

Parenterally administered compositions are formulated to allow for injection, either as a bolus or as a continuous infusion. Formulations for injection can be prepared in unit dosage forms, such as ampules, or in multi-dose units, with added preservatives. The compositions for injection can be in the form of suspensions, solutions, or emulsions, in either oily or aqueous vehicles. They may also contain formulatory agents such as suspending agents, stabilizing agents, and/or dispersing agents. The active ingredient may also be presented in powder form for reconstitution with a suitable vehicle before use. Specific examples of formulating agents for parenteral injection are found in the U.S. Pharmacopeia.

For rectal administration or vaginal administration, compositions for use in of the present invention can be formulated as suppositories, creams, gels, or retention enemas.

For dietary supplements, the extract can be added in concentrations up to 5% by weight and mixed according to methods routine in the art. Dietary supplements for animals can be prepared in a variety of forms including, but not limited to, liquid, powder, or solid pill forms. In the present invention, TF-2 can administered either alone or in combination with other phytochemicals known to affect tumor cell growth, where combining compounds or extracts would lead to synergistic effects. Examples of other phytochemicals which can be used in combination with TF-2 include, but are not limited to, resveratrol and its hydroxylated and methoxylated analogs, rosemary extract, green tea extracts, orange peel extracts, Mexican Bamboo, and Huzhang extracts.

The following non-limiting examples are provided to further illustrate the claimed invention.

EXAMPLE 1

Extraction of Black Tea

Theaflavin polyphenols were isolated and purified. Black tea powder (100 g) was soaked in hot water (1000 ml) for 10 minutes. After filtration, the filtrates were extracted with 300 ml of chloroform three times for decaffeination. The aqueous phase was collected and extracted twice with 300 ml of ethyl acetate. The combined ethyl acetate phases were washed with a 2.5% sodium bicarbonate solution (300 ml) followed by distilled water (500 ml). The crude theaflavins (1.5 to 3%) were obtained after evaporating ethyl acetate to dryness in a vacuum rotary evaporator.

EXAMPLE 2

Cell Culture

Normal human W138 (cell strain AG06814E, PDL=16) and the SV40 virally transformed W138 cells (cell strain AG07217) were obtained from Coriell Institute for Medical Research (Camden, N.J.). Human colon cancer cells, Caco-2 (ATCC #HTB-37) and the matched normal colon cells CCD-33Co (ATCC #CRL-1539) were obtained from the American Type Culture Collection (Rockville, Md.). Cells were cultured in Dulbecco's medium containing 10% fetal bovine serum at 37° C., 5% $CO_2$. For the proliferation assays, W138 and W138VA cells were plated at 2×105 cells per 35 mm dish in a complete growth medium with or without a tea polyphenol present. Cell growth was measured by counting viable cells using the Trypan Blue exclusion method. To assure that polyphenols did not degrade during incubation, the culture was replenished with fresh growth medium containing the test compounds once every other day. There was no evidence of degradation as shown by no difference in results by either method. Proliferation was monitored by crystal-violet staining. Cells were plated in a standard 24 well tissue culture plate at 1×105 cells/ml in the presence of tea polyphenols. On the fourth or fifth day after plating, cells were fixed with 5% trichloroacetic acid and stained with Bacto Gram Crystal Violet solution (Difco, Detroit, Mich.).

EXAMPLE 3

TUNEL Assay

Apoptosis was examined y in situ TUNEL assay using the Apoptosis Detection System (Promega, Madison, Wis.). Cultures at about 90% confluency were treated with TF-2 (100 μM) for 18 hours. Cells were fixed with 4% formaldehyde solution, then rehydrated, washed, and incubated in a buffer containing fluorescein-12-dUTP and terminal deoxynucleotidyl transferase for 1 hour. Cells were also stained with propidium iodide to stain the cytoplasm. The nuclei of apoptotic cells exhibited green fluorescence using an FITC filter under fluorescent microscope. All intact cells, including the apoptotic cells, were viewed using a rhodamine filter.

EXAMPLE 4

DNA Fragmentation Analysis

Confluent cultures were treated with TF-2 at 50 μM concentration for either 16, 24 or 30 hours or at 100 μM concentration for either 4, 12, 18, or 24 hours. At the indicated time points, cells were harvested and suspended in a lysis buffer (10 mM Tris HCl, pH 8.0, 100 mM NaCl, 25 mM EDTA, 0.5% SDS and 100 μg/ml proteinase K) for 20 hours at 37° C. DNA was extracted by phenol/chloroform/isoamyl alcohol (25:24:1). DNA was precipitated by 100% of ethanol, vacuum dried, and dissolved in a TE buffer (10 mM Tris HCl and 1 mM EDTA, pH 8.0). RNA in the sample was digested with 2 μg/ml of RNase Cocktail (Ambion, Austin, Tex.) for 30 minutes at 25° C. The DNA samples were analyzed by electrophoresis on a 1% agarose gel containing ethidium bromide (0.5 μg/ml).

EXAMPLE 5

Northern Blot Analysis

Confluent cultures were serum-deprived for 48 hours. Cells were then treated with 10% fresh fetal bovine serum in the presence or absence of the black tea extracts (10, 20, 40, 50, 80 or 100 μM) to initiate the progression of the cell cycle. Cells were harvested at either 4 or 12 hours for total RNA isolation. Total RNA samples were resolved by electrophoresis on 1% agarose-formaldehyde gel (6 μg per lane) and transferred onto a nylon membrane. Northern blot analysis was performed.

EXAMPLE 6

Reverse Transcription Polymerase Chain Reaction (RT-PCR) Assay

Confluent cultures were first serum-deprived for 48 hours and then stimulated with 10% fresh fetal bovine serum in the absence or presence of black tea extracts. Cells were harvested and total RNA was prepared using a kit (QIAGEN, Chatsworth, Calif.). Total RNA (1 μg) from each cell sample was reverse transcribed into cDNA by incubating with RNase H reverse transcriptase (Gibco BRL, Grand Island, N.Y.) using oligo(dT)$_{12-18}$ as primer. For PCR amplification, gene specific primers were designed. The sequences of the sense and antisense primers for various genes were:

anti-rabbit IgG conjugated to horseradish peroxidase was used as secondary antibody. The hybridized protein bands were detected using the ECL kit (Amersham Pharmacia, Piscataway, N.J.).

| | | |
|---|---|---|
| (HG3PDH sense) | 5'-TGAAGGTCGGAGTCAACGGATTTGGT-3' | (SEQ ID NO: 1) |
| (HG3PDH antisense) | 5'-CATGTGGGCCATGAGGTCCACCAC-3' | (SEQ ID NO: 2) |
| (BRCA1 sense) | 5'-CTCTGGGAAAGTATCGCTGTCATG-3' | SEQ ID NO: 3) |
| (BRCA1 antisense) | 5'-AGAGGCATCCAGAAAAGTATCAGG-3' | (SEQ ID NO: 4) |
| (BRCA2 sense) | 5'-TGCTGCCAGTAGAAATTCTC-3' | (SEQ ID NO: 5) |
| (BRCA2 antisense) | 5'-CTTTGTCCAAAGATTCCTTTG-3' | (SEQ ID NO: 6) |
| (ODC sense) | 5'-AATCAACCCAGCGTTGGACAA-3' | (SEQ ID NO: 7) |
| (ODC antisense) | 5'-ACATCACATAGTAGATCGTCG-3' | (SEQ ID NO: 8) |
| (TK sense) | 5'-AGCACAGAGTTGATGAGACGC-3' | (SEQ ID NO: 9) |
| (TK antisense) | 5'-GCTTCCTCTGGAAGGTCCCAT-3' | (SEQ ID NO: 10) |
| (PCNA sense) | 5'-ACGTCTCTTTGGTGCAGCTC-3' | (SEQ ID NO: 11) |
| (PCNA antisense) | 5'-CAAGTTGTTCAACATCTAAATCCATC-3' | (SEQ ID NO: 12) |
| (COX1 sense) | 5'-GTTCAACACCTCCATGTTGGTGGAC-3' | (SEQ ID NO: 13) |
| (COX1 antisense) | 5'-TGGTGTTGAGGCAGACCAGCTTC-3' | (SEQ ID NO: 14) |
| (COX2 sense) | 5'-TTCAAATGAGATTGTGGGAAAAT-3' | (SEQ ID NO: 15) |
| (COX2 antisense) | 5'-AGATCATCTCTGCCTGAGTATCTT-3' | (SEQ ID NO: 16) |
| (c-myc sense) | 5'-CAGGATCCGTGCATCGACCCCTCGGTG-3' | (SEQ ID NO: 17) |
| (c-myc antisense) | 5'-CGCCTAAGCTTTGACATTCTCCTCGGTG-5' | (SEQ ID NO: 18) |
| (c-jun sense) | 5'-CCAAGATCCTGAAACAGAGCATG-3' | (SEQ ID NO: 19) |
| (c-jun antisense) | 5'-TCCGAGTTCTGAGCTTTCAAGGT-3' | (SEQ ID NO: 20) |
| (c-fos sense) | 5'-ATGATGTTCTCGGGCTTCAACGCAG-3' | (SEQ ID NO: 21) |
| (c-fos antisense) | 5'-CCGAAGAAGCCAGGCTCTAGTTAGCG-3' | (SEQ ID NO: 22) |

PCR was performed under conditions that allowed the amounts of PCR products to be proportional to the amounts of RNA input. The housekeeping gene, glyceraldehyde-3-phosphate dehydrogenase (GAPDH) was used as an internal control. The PCR products were analyzed by electrophoresis on 1% agarose gel containing 0.5 µg/ml ethidium bromide.

EXAMPLE 7

Western Blot Analysis

Cells at 90% confluency were serum-deprived for 48 hours and then stimulated with fresh fetal bovine serum in the presence of various concentrations of TF-2 from 0 to 80 µM for 20 hours. Cells were harvested in a lysis buffer (150 mM NaCl, 100 mM Tris, pH 8.0, 1% Tween 20, 1 mM EDTA, 50 mM DDT, 1 mM PMSF, 10 µg/ml aprotinin, and 10 µg/ml leupeptin). The cell lysates were sonicated and centrifuged at 11,000×g for 10 minutes. The supernatant containing 30 µg of protein was analyzed on a 10% SDS-PAGE under reducing conditions. The gel was transferred onto a nitrocellulose membrane and the membrane was probed with anti-Cox2 antibody (Cayman Chemical, Ann Arbor, Mich.) at a 1:1000 dilution. The affinity purified goat

What is claimed is:

1. A method of treating or preventing inflammation in an animal comprising, administering orally to an animal in need thereof a composition comprising an ethyl acetate extract of black tea, said extract comprising theaflavin-3-gallate and theaflavin-3'-gallate in an amount effective to suppress Cyclooxygenase-2 (COX-2) gene expression in the animal so as to thereby treat or prevent inflammation in the animal.

2. The method of claim 1, wherein said composition further comprises a physiologically acceptable carrier or excipient.

3. The method of claim 1, wherein said composition is an oral composition.

4. The method of claim 1, wherein said composition is administered to said animal in a food.

5. The method of claim 1, wherein said composition is a nutraceutical.

6. The method of claim 1, wherein said composition is a dietary supplement.

7. The method of claim 1, wherein said composition is in the form of a capsule, a tablet, a lozenge or a coated tablet.

8. The method of claim 1, wherein said composition is in the form of a solution, a syrup, or a suspension.

9. The method of claim 8, wherein said theaflavin-3-gallate and theaflavin-3'-gallate are present in a total concentration of between 50 μM and 100 μM in said composition.

10. The method of claim 6, wherein said composition further comprises resveratrol, a hydroxylated resveratrol analog, a methoxylated resveratrol analog, a rosemary extract, a green tea extract, a orange peel extract, a Mexican bamboo extract, and/or a Huzhang extract.

11. The method of claim 5, wherein said composition further comprises resveratrol, a hydroxylated resveratrol analog, a methoxylated resveratrol analog, a rosemary extract, a green tea extract, a orange peel extract, a Mexican bamboo extract, and/or a Huzhang extract.

12. The method of claim 3, wherein said composition is formulated to provide controlled time release.

13. The method of claim 10, wherein said composition is formulated to provide controlled time release in the human.

14. The method of claim 11, wherein said composition is formulated to provide controlled time release.

15. The method of claim 6, wherein said theaflavin-3-gallate and theaflavin-3'-gallate are present in a total concentration of up to 5% by weight in said composition.

* * * * *